United States Patent [19]

Lefer

[11] 4,337,273

[45] Jun. 29, 1982

[54] METHODS OF INCREASING CORONARY BLOOD FLOW THROUGH VASODILATION BY FLURBIPROFEN

[75] Inventor: Allan M. Lefer, Montgomery, Pa.

[73] Assignee: Thomas Jefferson University, Philadelphia, Pa.

[21] Appl. No.: 234,681

[22] Filed: Feb. 17, 1981

Related U.S. Application Data

[62] Division of Ser. No. 150,048, May 15, 1980, Pat. No. 4,282,252.

[51] Int. Cl.$^3$ ............................................. A61K 31/19
[52] U.S. Cl. ................................................... 424/317
[58] Field of Search ........................................ 424/317

[56] References Cited

PUBLICATIONS

Chem. Abstrs. 84: 54062z, 1976; 83: 91077h, 1975.
Davies et al., "Ibuprofen: A Review of its Pharmacological Properties and Therapeutic Efficacy in Rheumatic Disorders", Drugs, 2:416–446, (1971).
Brooks et al., "Tolerance and Pharmacology of Ibuprofen", Current Therapeutic Research, vol. 15, No. 4, (Apr. 1973).
Jugdutt et al., "Infarct Size Reduction by Intravenous Ibuprofen After Coronary Occulsion in Conscious Dogs", American Journal of Cardiology, vol. 43, p. 393, (1979).
Maclean et al., "Long-Term Salvage of Ischemic Myocardium by Depleting Catecholamines and Inhibiting Inflammation", Clinical Research, vol. 25, p. 455A, (1977).
Lefer et al., "Beneficial Effects of Ibuprofen in Acute Myocardial Ischemia", Cardiology, 64:265–279, (1979).
Nishizawa et al., "Flurbiprofen, A New Potent Inhibitor of Platelet Aggregation", Thrombosis Research, 3:577–588, (1973).
Glenn et al., "The Pharmacology of 2-(2-Fluoro-4-Biphenylyl) Propionic Acid (Flurbiprofen) A Potent Non-Steroidal Anti-Inflammatory Drug", Agents and Actions, vol. 3/4:210–216, (1973).
Parratt et al., "The Effect of a New Anti-Inflammatory Drug, Flurbiprofen, on the Respiratory, Hemodynamic and Metabolic Responses to E. coli Endotoxin Shock in the Cat", British Journal of Pharmacology, vol. 58, pp. 547–551, (1976).
Darsee et al., "Lateral and Epicardial Ischemic Border Zone Salvage by Flurbiprofen Using an In Vivo Area-at-Risk Method", Federation Proceedings, Mar. 1, 1980, vol. 39:1112, (1980).
Lefer et al., "Mechanisms in the Optimal Protective Effects of Ibuprofen in Acute Myocardial Ischemia", Advances in Shock Research, 3:133–141, (1980).
"Optimal Dose of Ibuprofen in Acute Myocardial Ischemia in the Cat", Abstract No. 48, Present at Shock Society Meeting, Jun. 8, 1979.

Primary Examiner—Frank Cacciapaglia, Jr.
Attorney, Agent, or Firm—Woodcock, Washburn, Kurtz, Mackiewicz & Norris

[57] ABSTRACT

Novel treatments are disclosed for increasing circulating coronary blood flow. These treatments are useful for individuals who are expected to otherwise exhibit symptoms of reduced coronary circulation. Such individuals include those having coronary artery disease, angina, particularly unstable angina and Prinzmetal's angina, and coronary vasospasm. In accordance with the disclosed methods, coronary vasodilation is accomplished through the administration of effective amounts of ibuprofen and/or flurbiprofen. At the indicated dosages, thromboxane synthesis is effectively inhibited without inhibiting prostacyclin synthesis. Flurbiprofen administration additionally results in thromboxane antagonism.

5 Claims, No Drawings

METHODS OF INCREASING CORONARY BLOOD FLOW THROUGH VASODILATION BY FLURBIPROFEN

This is a division of application Ser. No. 150,048, filed May 15, 1980, now U.S. Pat. No. 4,282,252, which is hereby incorporated by reference.

BACKGROUND OF THE INVENTION

The present invention relates to methods for treating patients suffering from coronary artery disease, unstable angina, Prinzmetal's angina, and patients with a tendency towards coronary thrombosis and those having coronary vasospasm. More particularly, the present invention relates to treatments for those conditions through the administration of vasodilating agents.

A great need exists to develop safe, effective, long-term methods for treating the above mentioned conditions. Unlike myocardial infarction (MI), which is the substantially complete occlusion of a coronary artery by reason of its blockage with a clot or a thrombus, in the above mentioned conditions, persistent insufficient coronary artery flow stemming from restricted coronary lumen size results in periodic symptoms and a greater risk of coronary thrombosis.

One method of treating certain types of angina, coronary artery disease, coronary vasospasm, and other disease syndromes characterized by insufficient coronary blood flow is the periodic administration of coronary vasodilating substances. By dilating the coronary arteries of a given patient, increased blood flow may be obtained while reducing the probability that myocardial infarction may occur.

Of course, many factors must be considered prior to the chronic administration of a vasodilator. Most notably, all of the various side effects which might be produced as a result of that chronic administration should be considered prior to its selection for treatment of a given condition. For example, a good vasodilator for treating individuals exhibiting a higher risk of coronary thrombosis would be a substance which incidentally inhibited platelet aggregation and/or thromboxane synthesis, did not interfere with prostacyclin synthesis, and otherwise exhibited beneficial effects with respect to other disease syndromes, such as myocardial infarction, which might coincidently develop in the subject patient. Similarly, the vasodilator of choice might exhibit other beneficial side effects, such as analgesic or anti-inflammatory side effects, without producing dyspepsia (when orally administered), or other deleterious side effects which are often associated with anti-inflammatory agents such as aspirin, indomethacin or meclofenamate. An ideal vasodilator would also exhibit a high degree of coronary artery specificity, showing a minimal effect on systemic hemodynamics, such as systemic blood pressure.

To date, while numerous agents have been identified for administration as vasodilators, the effectiveness of these vasodilators when compared with the side effects caused by these vasodilators, has prevented many of these substances from gaining wide spread acceptance. Many drugs have been suggested as anti-inflammatory agents, typically for treating arthritis, or as agents which may be administered after the occurrence of a myocardial infarction. One such drug, ibuprofen, has been suggested for use either as an anti-inflammatory agent, or for immediate administration to patients who are suffering from myocardial infarction, to limit the spread of acute ischemic tissue. In particular, ibuprofen has been reported as being more active than aspirin in inhibiting experimentally-induced inflammations in animals and in suppressing experimentally-induced pain and fever. In "Ibuprofen: A Review of its Pharmacological Properties and Therapeutic Efficacy in Rheumatic Disorders", Elizabeth F. Davies and G. S. Avery, Drugs 2:416–446 (1971), it was suggested that ibuprofen has no glucocorticoid activity and only minor, and probably non-specific, effects on the cardiovascular system. Similarly, it was reported that the anti-inflammatory activity of ibuprofen shown in animals either does not exist in man, or is not detectable by present methods.

Later, in *Current Therapeutic Research*, Vol. 15, No. 4 (April, 1973) in an article entitled "Tolerance and Pharmacology of Ibuprofen", by Brooks et al, ibuprofen [2-(4-isobutylphenylpropionic acid)] is reported as an analgesic, anti-inflammatory compound which is non-toxic, well-tolerated, capable of controlling symptoms in rheumatoid arthritics, an inhibitor of platelet aggregation capable of prolonging bleeding time, and at higher doses, a protector against skin inflammation by tetrahydrofurfuryl nicotinate.

Even more recently, in an abstract appearing in *Clinical Research*, Vol. 25, page 455A (1977), entitled "Long-Term Salvage of Ischemic Myocardium by Depleting Catecholamines and Inhibiting Inflammation", Maclean et al, it was suggested that myocardial infarct size and thickness may be reduced through three post-occlusion, intramuscular injections of ibuprofen at 50 mg/kg. In this study, myocardial infarct size was measured by total left ventricular creatine kinase depression and by quantitative histology performed two and twenty-one days afer occlusion of the left coronary artery in rats.

As recently as 1979, in an abstract entitled "Infarct Size Reduction by Intravenous Ibuprofen After Coronary Occulsion in Conscious Dogs", Jugdutt et al, *American Journal of Cardiology*, Vol. 43, page 393 (1979), the post-occlusion intravenous administration of 6 mg/kg/hr of ibuprofen in dogs having occluded coronary arteries was reported as altering the masses of infarct and risk region so that dogs with similar risk regions had smaller infarcts. Collateral blood flow increases and resistance decreases were reported over the six hour post-occlusion test period in both the control and ibuprofen treated groups, which changes did not differ significantly between groups. The authors concluded that the protection of Ibuprofen was "not explained by changes in collateral flow, heart rate and blood pressure and may be due to beneficial metabolic and cellular properties of ibuprofen outweighing deleterious effects of prostaglandin inhibition".

See also, "Beneficial Effects of Ibuprofen in Acute Myocardial Ischemia", Lefer and Polansky, *Cardiology* 64:265–279 (1979), wherein post-occlusion intravenous ibuprofen administration at a rate of 12.5 mg/kg is reported as preventing the loss of myocardial creatine phosphokinase, of returning S-T segment elevation toward normal values, and significantly preventing the myocardial loss of compounds having free amino nitrogen groups, the protective mechanism of ibuprofen being described as a stabilization of cellular membranes and to a lesser extent a reduction in myocardial oxygen demand.

Thus, while ibuprofen has been the topic of numerous studies to determine its pharmacologic effects, ibuprofen has not been reported as having any significant effect on the coronary vasculature, or for use in cardiologic treatments, other than as an agent administered after experimentally induced myocardial infarctions, i.e., following intentional, complete coronary artery occlusion.

Another drug which has received some attention in the literature is flurbiprofen. In an article entitled "Flurbiprofen, A New Potent Inhibitor of Platelet Aggregation", Nishizawa, et al, *Thrombosis Research* 3:577–588 (1973), flurbiprofen [dl-2-(2-fluoro-4-biphenylyl) propionic acid] is described as a non-steroidal anti-inflammatory compound whose inhibitory activity on collagen-induced platelet aggregation approaches the activity seen with prostaglandin $E_1(PGE_1)$. Oral administration of flurbiprofen is described as being without side effects at various doses, and of exhibiting anti-aggregating effects, of prolonging mesenteric bleeding time in rats, and as preventing death in mice due to pulmonary thromboembolisms produced by collagen injection. The authors concluded that flurbiprofen might be "promising potential antithrombotic agent," and suggested that prolonged bleeding times might suggest flurbiprofen to be an inhibitor of thrombus formation, and to be capable of preventing death due to pulmonary congestion by platelet emboli following infusion of collagen.

Later, in a paper appearing in *Agents and Actions*, Vol. 3/4:210–216 (1973), entitled "The Pharmacology of 2-(2-Fluoro-4-Biphenylyl) Propionic Acid (Flurbiprofen) A Potent Non-Steroidal Anti-Inflammatory Drug", Glenn, et al, flurbiprofen was described as having a potent and prolonged anti-inflammatory action. Recently, a paper entitled "The Effect of a New Anti-Inflammatory Drug, Flurbiprofen, on the Respiratory, Hemodynamic and Metabolic Responses to E. coli Endotoxin Shock in the Cat", Parratt and Sturgess, *British Journal of Pharmacology*, Vol. 58, pages 547–551 (1976), prior intravenous administration of flurbiprofen in doses of 100 and 250 ug/kg and 1.0 mg/kg were described as abolishing or greatly reducing the immediate pulmonary hypertension and reductions in lung compliance and systemic arterial $PO_2$. At page 549, the direct effects of sodium flurbiprofen at doses of 0.1, 0.25 and 1.0 mg/kg were described as not being significant on systemic arterial pressure and dP/dt max, pulmonary artery pressure, heart rate, cardiac output, intratracheal pressure or lung compliance. Flurbiprofen was also described as being without significant effect on arterial lactate, glucose, pH, or $PO_2$.

More recently, in an abstract published in the *Federation Proceedings*, March 1, 1980, Vol. 39:1112 (1980) entitled "Lateral and Epicardial Ischemic Border Zone Salvage by Flurbiprofen Using an In Vivo Area-At-Risk Method", by Darsee, et al, flurbiprofen administered at a rate of 1 mg/kg intravenously at 30 minutes and 4 hours after left anterior descending coronary artery occlusion was reported as aiding in both lateral and epicardial salvage in the flurbiprofen treated dogs.

As seen from the above, flurbiprofen has not been reported as having any in vivo or in vitro effects on the coronary vasculature.

SUMMARY OF THE INVENTION

The present invention provides novel methods for treating angina, particularly unstable and Prinzmetal's forms of angina, patients with a tendency towards coronary thrombosis, such as those patients suffering from atherosclerosis or coronary stenosis, and those having coronary vasospasm. In accordance with these methods, protective amounts of ibuprofen or flurbiprofen are administered to the coronary arteries to cause coronary vasodilation. These administrations do not inhibit prostacyclin synthesis and do not substantially alter systemic blood pressure or heart rate. Administration of these compounds, and particularly ibuprofen, coincidentally inhibit thromboxane and other prostaglandin synthesis. Antagonism of thromboxane synthesis may also result when flurbiprofen is administered. Accordingly, the methods of the present invention accomplish coronary vasodilation utilizing heretofore unknown vasodilating compounds which effectively relieve the symptoms of reduced coronary blood flow, and coincidentally exhibit beneficial side effects.

Accordingly, a primary object of the present invention is the provision of treatments for individuals suffering from conditions of restricted coronary circulation, such as coronary artery disease, angina, particularly unstable angina or Prinzmetal's angina, atherosclerosis, coronary stenosis, and those having coronary vasospasm.

This, and other objects of the present invention will become apparent from the following more detailed description.

DESCRIPTION OF THE PREFERRED EMBODIMENTS

In accordance with the preferred embodiments of the present invention, novel methods for treating angina, particularly unstable and Prinzmetal's forms of angina, atherosclerosis, coronary stenosis, and coronary vasospasm are provided. According to these methods, protective administrations of ibuprofen or flurbiprofen through oral or intravenous routes are utilized to cause coronary vasodilation without inhibiting prostacyclin synthesis and without substantially altering systemic blood pressure or heart rate.

It has been found that at blood plasma concentrations of 20–200 ug/ml, ibuprofen and its pharmaceutically acceptable salts (such as sodium ibuprofen), produce concentration-dependent decreases in coronary perfusion pressure at constant flow rates which are indicative of vasodilation. While the degree of vasodilation at 25 ug/ml was found to be only 3–5 mmHg for a typical perfused cat coronary artery, this degree of vasodilation is nonetheless indicative of a threshold response. As concentrations of ibuprofen are increased from the threshold minimum of 20 to 25 ug/ml to 200 ug/ml, vasodilator responses increase to within the range of about 8 to 25 mmHg.

In accordance with the ibuprofen methods of the present invention, patients who exhibit symptoms of insufficient coronary circulation, such as those having angina, particularly unstable angina or Prinzmetal's angina, atherosclerosis, coronary stenosis, coronary artery disease, and/or coronary vasospasm, and who would thus benefit from coronary vasodilation, receive administrations of between 1.5 and 12 mg/kg of ibuprofen. Since lower dosages of ibuprofen do not drastically interfere with the production of prostacyclin, an aggregation inhibitor, preferred dosages are in the range of 3 to 6 mg/kg of body weight. In accordance with the methods of present invention, ibuprofen is administered prior to symptom onset at least on a daily basis, either orally or intravenously, to establish and maintain plasma levels within the range of 20 ug/ml to 200 ug/ml, more particularly about 50-100 ug/ml.

For additional information relating to ibuprofen administration, please refer to U.S. Pat. No. 4,282,252 and to "Mechanisms in the Optimal Protective Effects of Ibuprofen in Acute Myocardial Ischemia" by Allan M. Lefer and Karen Crossley, *Advances in Shock Research* 3:133-141 (1980), which paper is hereby incorporated by reference as if fully set forth herein.

In accordance with the flurbiprofen embodiment of the present invention, flurbiprofen is administered orally or intravenously at rates of 0.75 to 6 mg/kg, preferably 1-3 mg/kg of body weight. Testing of administrations of flurbiprofen in the same manner as described above for ibuprofen on 8 cat coronary arteries perfused at constant flow has indicated that the administration of 10 ug/ml of flurbiprofen produces a pressure drop of 5±1 mmHg. Testing of nine cat coronary arteries with concentrations of flurbiprofen at 50 ug/ml resulted in a pressure drop of 27±6 mmHg, while testing of seven cat coronary arteries with flurbiprofen concentrations of 100 ug/ml produced a pressure drop of 35±4 mmHg. In accordance with the preferred flurbiprofen embodiment of the present invention, flurbiprofen (or its pharmaceutically acceptable salts) is periodically administered to maintain plasma levels of between 10 and 100 ug/ml of flurbiprofen, preferably between about 17 and 50 ug/ml of flurbiprofen. In addition to exhibiting a vasodilating effect, administrations of flurbiprofen have been found to be thromboxane antagonists. In this regard, cat coronary arteries were perfused at constant flow rates with solutions containing 5 nanograms/ml of $CTA_2$, a potent synthetic thromboxane vasoconstrictor. When $CTA_2$ was applied alone for eight cat coronary arteries during constant flow rate perfusion, pressures increased by 40±3 mmHg. Administrations of a similar concentration of $CTA_2$ and flurbiprofen at 100 mg/ml produced an increase of only 2±2 mmHg on eight similarly perfused cat coronary arteries. Accordingly, it may be concluded that flurbiprofen is a potent thromboxane antagonist which not only causes vasodilation but also has the ability to reverse thromboxane induced coronary vasoconstriction.

In view of the above, it will be apparent that an extremely simple, non-toxic vasodilating approach is provided which is useful in treating conditions of restricted coronary blood flow, such as occur in individuals having atherosclerosis, coronary stenosis, angina, principally unstable and Prinzmetal's forms of angina, and coronary artery disease. As one of ordinary skill in the art will readily appreciate, the methods of the present invention are useful in those conditions where coronary blood flow is restricted, as for example by reason of vasospasm, but not to conditions wherein vasodilation is unlikely to have a substantial effect, such as where coronary arteries are occluded by blockages, such as clots or coronary embolisms, which may be lodged therein. Accordingly, it is not within the scope of the present invention to administer ibuprofen or flurbiprofen after the occurrence of such blockages or the symptoms caused thereby.

As seen from the above, extremely simple, inexpensive preventative treatments are provided to relieve the symptoms of the above-enumerated disease syndromes. These treatments represent substantial advances over those vasodilating treatments heretofore known to the art.

What is claimed is:

1. A method of treating a patient suffering from angina, coronary heart disease, or coronary vasospasm, and who exhibits periodic symptoms of reduced coronary blood flow, which comprises administering to said patient an amount of flurbiprofen effective to cause dilation of the coronary arteries of said patient, whereby coronary blood flow is substantially increased.

2. The method of claim 1, wherein said administration comprises the step of orally administering from 0.75 to 6 mg/kg of body weight of flurbiprofen prior to the onset of said symptoms.

3. The method of claim 2, wherein said step of administration further comprises orally administering flurbiprofen in the amount of 1-3 mg of flurbiprofen per kilogram of said patient's body weight.

4. The method of claim 1, wherein said step of administering flurbiprofen comprises the step of introducing said flurbiprofen into said patient's bloodstream to achieve circulating coronary artery blood plasma levels of flurbiprofen from 10 ug/ml to 100 ug/ml.

5. The method of claim 4, wherein said step of administering further comprises achieving circulating coronary artery blood plasma levels of flurbiprofen of from 17-50 ug/ml.

* * * * *